US011028124B2

(12) United States Patent
Bransby

(10) Patent No.: US 11,028,124 B2
(45) Date of Patent: Jun. 8, 2021

(54) METHODS, DEVICES AND SYSTEMS FOR 3-STAGE FILTRATION

(71) Applicant: REPLIGEN CORPORATION, Waltham, MA (US)

(72) Inventor: Michael Bransby, Waltham, MA (US)

(73) Assignee: Repligen Corporation, Waltham, MA (US)

( * ) Notice: Subject to any disclaimer, the term of this patent is extended or adjusted under 35 U.S.C. 154(b) by 342 days.

(21) Appl. No.: 15/972,442

(22) Filed: May 7, 2018

(65) Prior Publication Data

US 2019/0337979 A1    Nov. 7, 2019

(51) Int. Cl.
*C07K 1/36* (2006.01)
*B01D 63/02* (2006.01)
*B01D 69/08* (2006.01)

(52) U.S. Cl.
CPC ............ *C07K 1/36* (2013.01); *B01D 63/02* (2013.01); *B01D 69/08* (2013.01); *B01D 2315/14* (2013.01); *B01D 2317/022* (2013.01); *B01D 2317/025* (2013.01)

(58) Field of Classification Search
None
See application file for complete search history.

(56) References Cited

U.S. PATENT DOCUMENTS

| | | | |
|---|---|---|---|
| 6,080,571 A | 6/2000 | Prior et al. | |
| 6,383,380 B1 | 5/2002 | Kopf | |
| 7,763,666 B2 | 7/2010 | Vero et al. | |
| 8,668,886 B2 | 3/2014 | Niazi | |
| 2001/0043916 A1 | 11/2001 | McNeilly et al. | |
| 2019/0322975 A1* | 10/2019 | Nakai | B01D 61/142 |

FOREIGN PATENT DOCUMENTS

WO    2000035567    6/2000

OTHER PUBLICATIONS

International Search Report and Written Opinion dated Jul. 19, 2019 for PCT/US19/31087 filed May 7, 2019.

* cited by examiner

*Primary Examiner* — David C Mellon
(74) *Attorney, Agent, or Firm* — Kacvinsky Daisak Bluni PLLC

(57) ABSTRACT

The present disclosure pertains to filtration methods comprising: passing a first fluid that comprises cells, cell debris and targeted product produced by the cells through a first filter thereby separating the first fluid into a first retentate comprising cells and a first permeate comprising targeted product and cell debris; combining resin beads having affinity for targeted product with the first permeate to form a second fluid containing resin beads with bound target product and cell debris; passing the second fluid through a second filter thereby separating the second fluid into a second retentate comprising resin beads with bound target product and a second permeate comprising cell debris; combining an elution buffer with the second retentate to form a third fluid that comprises a mixture of resin beads and unbound targeted product; and passing the third fluid through a third filter thereby separating resin beads from targeted product.

21 Claims, 6 Drawing Sheets

METHODS, DEVICES AND SYSTEMS FOR 3-STAGE FILTRATION

FIELD

The present disclosure relates to methods, devices and systems for filtration of biological fluids, including filtration of bioreactor fluids.

BACKGROUND

In aspects, the present disclosure pertains to filtration of bioreactor fluids. Bioreactor systems provide an environment supporting biological activity, which results in the build-up of cell metabolites, including metabolic waste, in the bioreactor fluid. The buildup of metabolic waste limits cell amplification or cell growth within the bioreactor. As a result, known high capacity bioreactor systems generally require either a very large and expensive bioreactor or require filtering bioreactor fluids to continue the biological activity.

In this regard, systems are known in which bioreactor fluid is cycled through a hollow fiber tangential flow filter which separates expressed proteins and metabolic waste from cells produced in the bioreactor, which cells are returned to the bioreactor, improving cell production in the bioreactor (see, e.g., U.S. Patent Pub. No. 2016/0222337 to Serway and Patent No. WO 2017/180573 to Serway et al.).

The use of 1.0 μm up to 5.0 μm thick wall hollow fiber tangential flow filters employed in systems of this type have been shown to consistently pass nearly 100% of monoclonal-antibody-sized proteins for harvest from cell culture. However, a certain amount of cell debris also passes through such filters along with the protein. Therefore, a polishing filter is typically used to further separate the cell debris from the protein.

The present disclosure provides methods, devices and systems for separating such cell debris from products of interest, including expressed target proteins, such as monoclonal antibodies, among others.

SUMMARY

In various aspects the present disclosure pertains to filtration methods that comprise: (a) passing a first fluid that comprises cells, cell debris and a targeted product produced by the cells through a first filter such that the first fluid is separated by the first filter into a first retentate comprising the cells and a first permeate comprising the targeted product and a first portion of the cell debris that passes through the first filter; (b) combining resin beads having affinity for the targeted product with the first permeate such that a second fluid is formed that comprises the resin beads with bound target product and the first portion of the cell debris; and (c) passing the second fluid through a second filter such that the second fluid is separated by the second filter into a second retentate comprising the resin beads with the bound target product and second permeate comprising a second portion of the cell debris that passes through the second filter.

In various embodiments, the method further comprises: combining an elution buffer with the second retentate such that the targeted product becomes unbound from the resin beads and a third fluid is formed that comprises a mixture of the resin beads and the targeted product; and passing the third fluid through a third filter such that the third fluid is separated by the third filter into a third retentate comprising the resin beads and a third permeate comprising the targeted product.

In various embodiments, which can be used in conjunction with the above aspects and embodiments, the second retentate is directly combined with the elution buffer. In these embodiments, the method may further comprise washing the second retentate by a process wherein the second retentate is mixed with a washing solution and subjected to additional filtration to further reduce the amount of cell debris in the second retentate before combining with the elution buffer.

In various embodiments, which can be used in conjunction with the above aspects and embodiments, the process is a batch process. In certain of these embodiments, (a) the resin beads and the first permeate are combined in a first batch mixer and/or (b) the elution buffer and the second retentate are combined in a second batch mixer.

In various embodiments, which can be used in conjunction with the above aspects and embodiments, the process is a continuous process. In certain of these embodiments, the second fluid is passed through a first static mixer prior to passage through the second filter and/or the third fluid is passed through a third static mixer prior to passage through the second filter.

In various embodiments, which can be used in conjunction with the above aspects and embodiments, the method further comprises regenerating the resin beads in the third retentate.

In various embodiments, which can be used in conjunction with the above aspects and embodiments, the targeted product is a protein. In certain of these embodiments, the targeted product a monoclonal antibody or a polyclonal antibody.

In various embodiments, which can be used in conjunction with the above aspects and embodiments, the resin beads are functionalized with one or more ligands selected from Protein A, Protein G, Protein A/G, and Protein L.

In various embodiments, which can be used in conjunction with the above aspects and embodiments, the first filter has a mean pore size ranging from 1 μm to 8 μm.

In various embodiments, which can be used in conjunction with the above aspects and embodiments, the first filter is a first tangential flow filter. In certain of these embodiments, the first tangential flow filter comprises hollow fibers having an inner lumen diameter ranging from 1 mm to 7 mm and a wall thickness of 1 mm to 8 mm.

In various embodiments, which can be used in conjunction with the above aspects and embodiments, the second filter has a mean pore size ranging from 2 μm to 30 μm.

In various embodiments, which can be used in conjunction with the above aspects and embodiments, the second filter is a second tangential flow filter. In certain of these embodiments, the second tangential flow filter comprises hollow fibers having an inner lumen diameter ranging from 1 mm to 7 mm and a wall thickness of 1 mm to 8 mm.

In various embodiments, which can be used in conjunction with the above aspects and embodiments, the third filter has a mean pore size ranging from 2 μm to 30 μm.

In various embodiments, which can be used in conjunction with the above aspects and embodiments, the third filter is a third tangential flow filter. In certain embodiments, the third tangential flow filter comprises hollow fibers having an inner lumen diameter ranging from 1 mm to 7 mm and a wall thickness of 1 mm to 8 mm.

BRIEF DESCRIPTION THE DRAWINGS

The above and other aspects of the present disclosure will be more apparent from the following detailed description, presented in conjunction with the following drawings wherein.

DETAILED DESCRIPTION

Figure 1A:
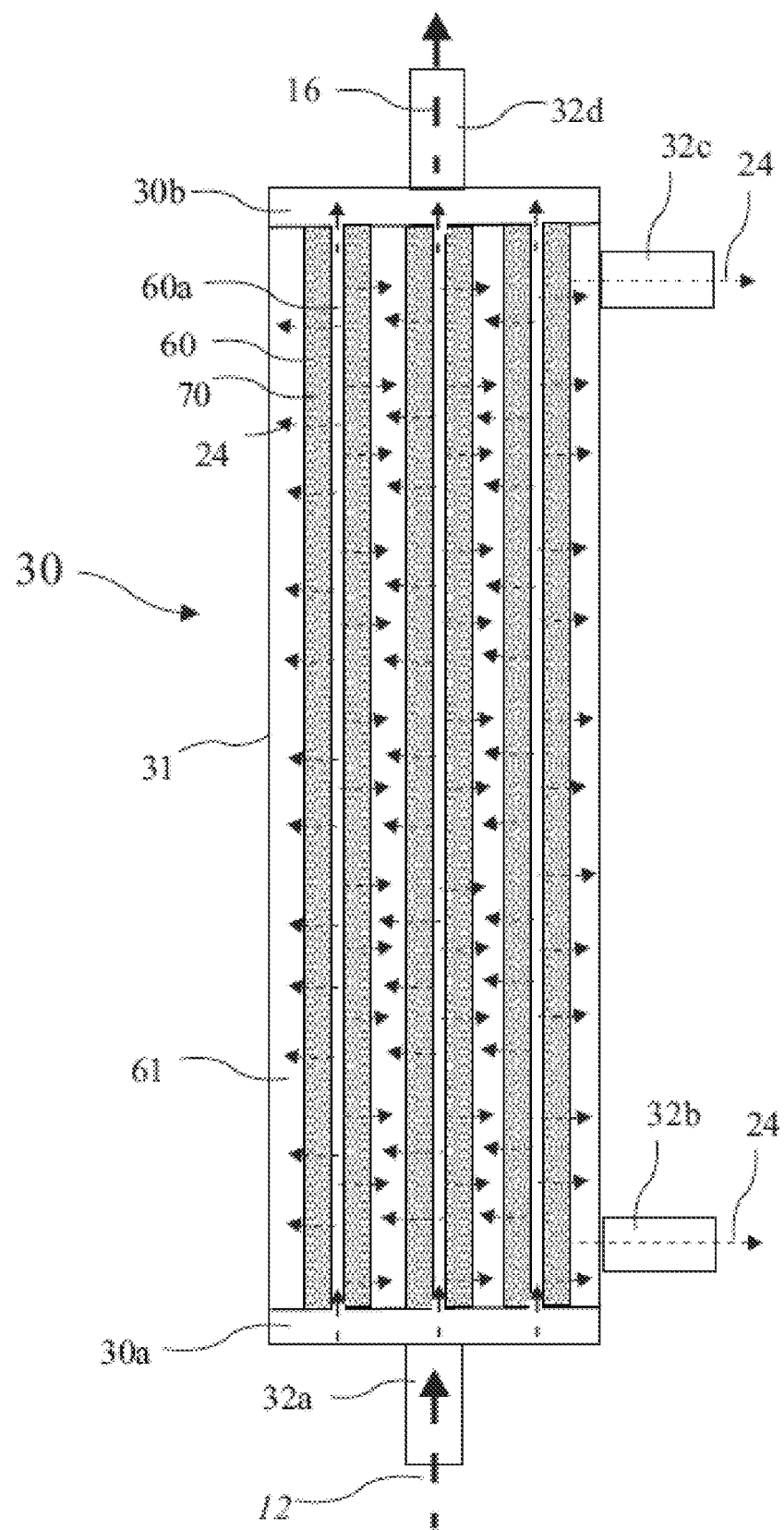
FIG. 1A is a schematic cross-sectional view of a hollow fiber tangential flow filter according to the present disclosure.

A schematic cross-sectional view of a hollow fiber tangential flow filter 30 finding use in conjunction with present disclosure is shown in FIG. 1A. The hollow fiber tangential flow filter 30 includes parallel hollow fibers 60 extending between an inlet chamber 30a and an outlet chamber 30b. A fluid inlet port 32a provides a flow 12 to the inlet chamber 30a and an retentate fluid outlet port 32d receives a retentate flow 16 from the outlet chamber 30b. The hollow fibers 60 receive the flow 12 through the inlet chamber 30a. The flow 12 is introduced into a hollow fiber interior 60a of each of the hollow fibers 60, and a permeate flow 24 passes through walls 70 of the hollow fibers 60 into a permeate chamber 61 within a filter housing 31. The permeate flow 24 travels to permeate fluid outlet ports 32b and 32c. Although two permeate fluid outlet ports 32b and 32c are employed to remove permeate flow 24 in FIG. 1A, in other embodiments, only a single permeate fluid outlet port may be employed. Filtered retentate flow 16 moves from the hollow fibers 60 into the outlet chamber 30b and is released from the hollow fiber tangential flow filter 30 through retentate fluid outlet port 32d.

Figure 1B:
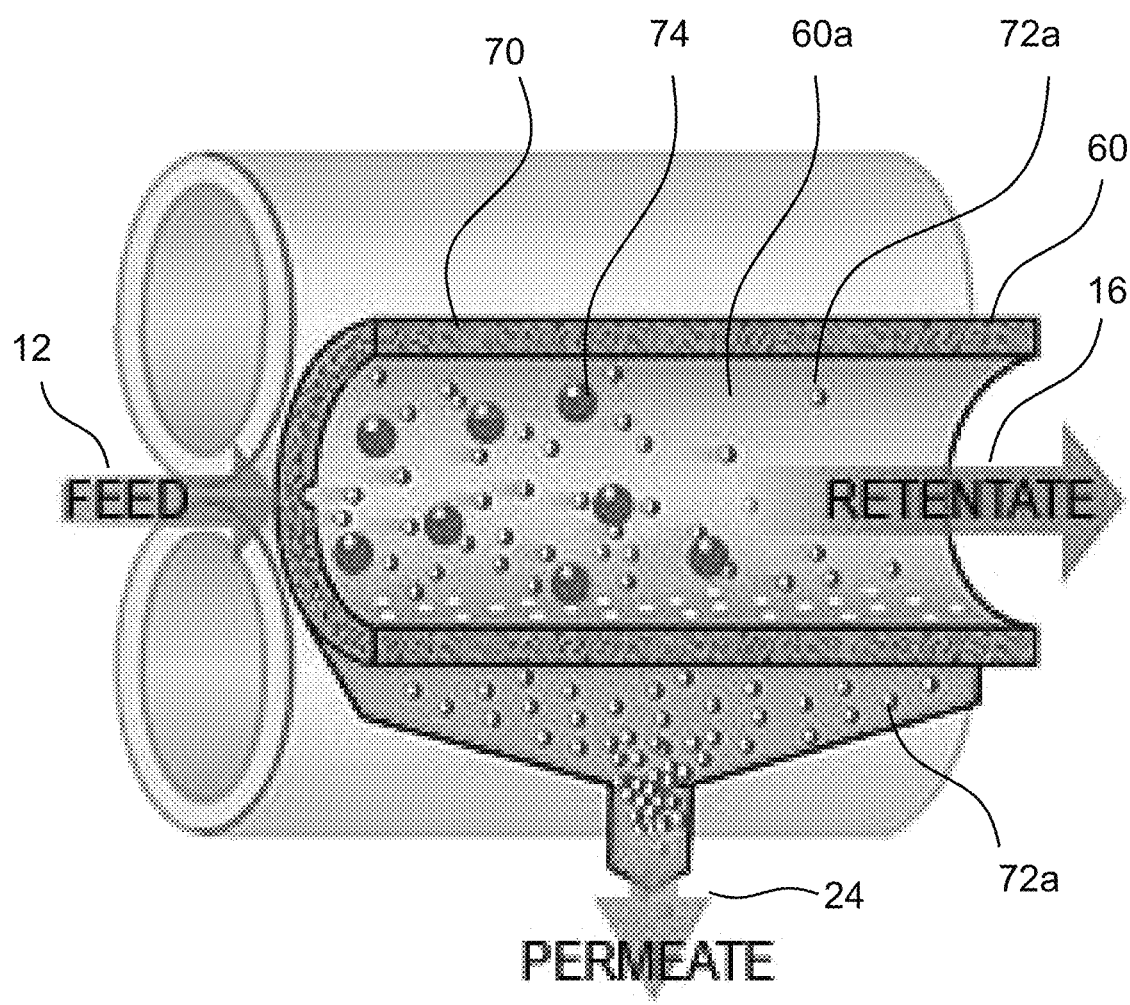
FIG. 1B is a schematic partial cross-sectional view of three hollow fibers within a tangential flow filter like that shown in FIG. 1A.

FIG. 1B is a schematic partial cross-sectional view of three hollow fibers 60 within a hollow fiber tangential flow filter analogous to that shown in FIG. 1A, and shows the separation of an inlet flow 12 (also referred to as a feed) which contains large particles 74 and target protein 44 into a permeate flow 24 containing a portion of the small particles and a retentate flow 16 containing the large particles 74 and a portion of the target protein 44 that does not pass through the walls 70 of the follow fibers 60.

Flow 12 may be created by any suitable pump including, for example, peristaltic pumps, positive displacement pumps, and pumps with levitating rotors inside the pumpheads, among others. In some embodiments, one or more pumps may be employed which include a low shear, gamma-radiation stable, disposable, levitating pumphead, for example, a model number PURALEV® 200SU low shear re-circulation pump manufactured by Levitronix, Waltham, Mass., USA. The PURALEV® 200SU includes a magnetically levitated rotor inside a disposable pumphead, and stator windings in the pump body, allowing simple removal and replacement of the pumphead.

A 3-stage tangential flow filtration method will now be briefly described. In a first filtration stage, bioreactor fluid, which contains, for example, cells, cell debris, expressed target protein and is passed through a first tangential flow filter to separate the target protein from the cells and cellular debris. However, a portion of the cellular debris passes through the first filtration stage. In a second stage, the cell debris passing through the first filter with the target protein is removed from the target protein by first binding the target protein to resin beads having affinity for the target protein, followed by filtration in a second filter, to separate the resin beads with bound target protein from the cell debris. In a third stage, the target protein is unbound from the resin beads using a suitable elution buffer, followed by filtration in a third tangential flow filter, to separate the resin beads from the unbound target protein. Each of these stages will now be detailed in turn.

Figure 2:
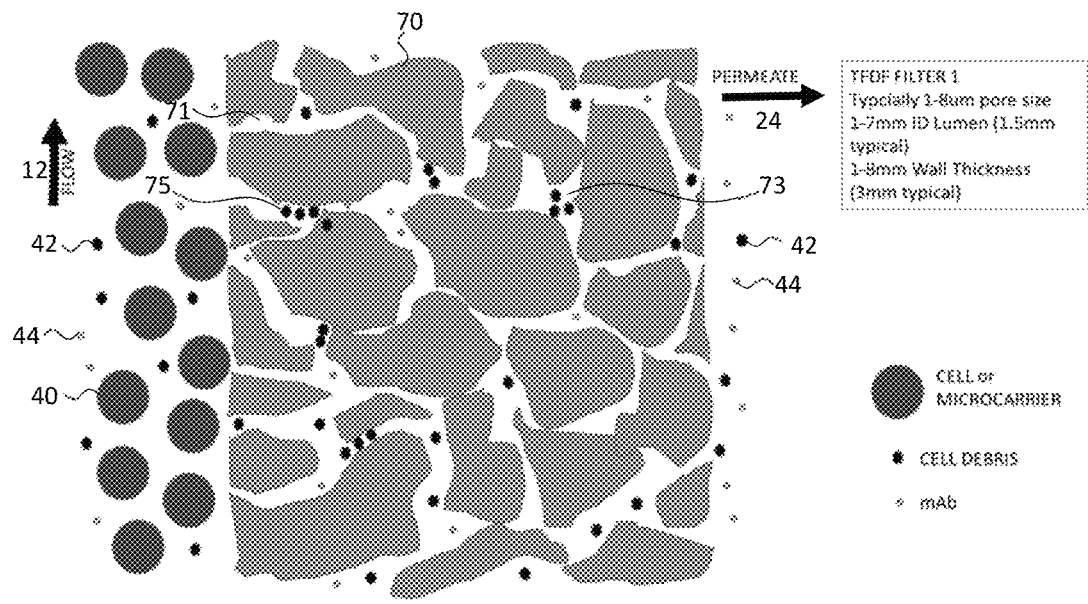
FIG. 2 is a schematic partial cross-sectional view of a wall of a hollow fiber within a tangential flow filter like that shown in FIG. 1A during a first filtration stage.

FIG. 2 is a schematic illustration of the first tangential flow filtration process in which a mixture which contains cells 40, cell debris 42, and target protein 44 (for purposes of illustration a monoclonal antibody, mAb, is described; however, the process applies to essentially any target protein) is passed through a first tangential flow filter (a filter wall 70 is shown, e.g., a wall 70 of a hollow fiber of a hollow fiber tangential flow filter like that of FIG. 1A) to separate the cells 40, which flow along the surface of the filter wall 70 and emerge from the filter in a retentate that is recycled to a bioreactor, from the target protein 44, which passes through the filter wall 70 via pores in the filter wall to form a permeate. A portion of the cell debris 42 also passes through the filter wall 70 and is present in the permeate, as well as other components including metabolic waste (not illustrated).

In general, any filtration system may be used, so long as the filtration system is able to separate the cells 40 from the target protein 44.

In various embodiments, the filter is a of hollow fiber tangential flow depth filter. With continued reference to FIGS. 1A and 2, an inlet flow 12 comprising cells 40, target protein 44, and cell debris 42 is introduced into an inlet port of a hollow fiber tangential flow depth filter 30. The cells 40 pass along the inner surface of the wall 70 that forms the hollow fiber interior 60a of the hollow fibers and are ultimately released in the retentate flow. The wall 70 includes tortuous paths 71 that capture certain elements (e.g., cell debris 42) of the flow 12 as a portion of the flow 12 passes through the wall 70 of hollow fiber tangential flow filter 30 while allowing other particles (e.g., target protein 44) to pass through the wall 70 as part of the permeate flow 24. In the schematic cross-sectional illustration of FIG. 2, settling zones 73 and narrowing channels 75 are illustrated as capturing cell debris 42 which enter the tortuous paths 71, while allowing target protein 44 to pass through the wall 70, thus trapping cell debris 42 and causing a separation of the cell debris 42 from target protein 44 in the permeate flow 24. This method is thus different from filtering obtained by the surface of thin wall hollow fiber tangential flow filter membranes, wherein cell debris 42 can build up at the inner surface of the wall 70, clogging entrances to the tortuous paths 71.

In this regard, one of the most problematic areas for various filtration processes, including filtration of cell culture fluids such as those filtered in perfusion and harvest of cell culture fluids, is decreased mass transfer of target molecule or particle due to filter fouling. The filters described herein overcome many of these hurdles by combining the advantages of tangential flow filtration with the advantages of depth filtration. As in standard thin wall hollow fiber filters using tangential flow filtration, cells are pumped through the lumens of the hollow fibers, sweeping them along the surface of the inner surface of the hollow fibers, allowing them to be recycled for further production. However, instead of the protein and cell debris forming a fouling gel layer at the inner surface of the hollow fibers, the wall adds what is referred to herein as a "depth filtration" feature that traps the cell debris inside the wall structure, enabling increased volumetric throughput while maintaining close to 100% passage of typical target proteins, in various embodiments of the disclosure. Such filters are referred to herein as tangential flow depth filters.

As illustrated schematically in FIG. 2, tangential flow depth filters in accordance with various embodiments of the present disclosure do not have a precisely defined pore structure. Particles that are larger than the "pore size" of the filter will be stopped at the surface of the filter. A significant quantity of intermediate-sized particles (e.g., cellular debris), on the other hand, enter the wall for the filter, and are entrapped within the wall before emerging from the opposing surface of the wall. Smaller particles and soluble materials can pass though the filter material in the permeate flow. Being of thicker construction and higher porosity that many other filters in the art, the filters can exhibit enhanced flow rates and what is known in the filtration art as "dirt loading capacity," which is the quantity of particulate matter a filter can trap and hold before a maximum allowable back pressure is reached.

In certain embodiments, a first tangential flow filter may be provided that employs thick wall hollow fibers having an inner lumen diameter ranging from 1 mm to 7 mm, typically about 1 mm to 2 mm, and a wall thickness of 1 mm to 8 mm, typically about 2 mm to 3 mm. In certain embodiments, a first tangential flow filter employing thick wall hollow fibers having a mean pore size ranging from 1 μm to 8 μm, typically ranging from 1 μm to 2 μm, may be used.

Although a single second tangential flow filter is described above for the first filtration stage, multiple filters may also be provided at this stage. For example, multiple filters may be provided in parallel to increase capacity.

Despite a lack of a precisely defined pore structure, the pore size of a given filter can be objectively determined via a widely used method of pore size detection known as the "bubble point test" The bubble point test is based on the fact that, for a given fluid and pore size, with constant wetting, the pressure required to force an air bubble through a pore is inversely proportional to the pore diameter. In practice, this means that the largest pore size of a filter can be established by wetting the filter material with a fluid and measuring the pressure at which a continuous stream of bubbles is first seen downstream of the wetted filter under gas pressure. The point at which a first stream of bubbles emerges from the filter material is a reflection of the largest pore(s) in the filter material, with the relationship between pressure and pore size being based on Poiseuille's law which can be simplified to $P=K/d$, where P is the gas pressure at the time of emergence of the stream of bubbles, K is an empirical constant dependent on the filter material, and d is pore diameter, in this regard, pore sizes determined experimentally herein are measured using a POROLUX™ 1000 Porometer (Porometer NV, Belgium), based on a pressure scan method (where increasing pressure and the resulting gas flow are measured continuously during a test), which provides data that can be used to obtain information on the first bubble point size (FBP), mean flow pore size (IMP) (also referred to herein as "mean pore size"), and smallest pore size (SP). These parameters are well known in the capillary flow porometry art.

Figure 3:
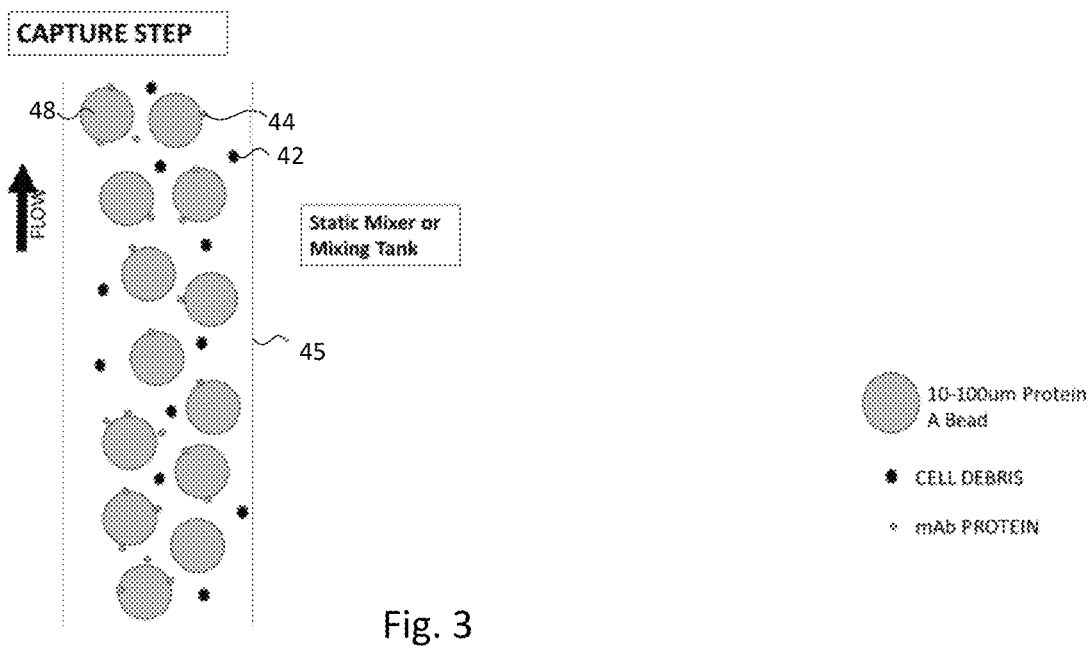
FIG. 3 is a schematic illustration of a capture step, in accordance with an embodiment of the present disclosure.

Turning now to FIG. 3, in a second stage the permeate from the first tangential flow filtration process of FIG. 2 is combined with resin beads 48 having affinity to the target protein 44, such that the target protein 44 is bound to the resin beads 48. A bead diameter is selected which is larger than the cell debris and may typically range from 1 μm to 100 μm, more typically ranging from 20 μm to 60 μm. The resin beads 48 may formed from various materials including polymeric materials, for example, polysaccharides such as agarose, or poly(styrene divinylbenzene), among others.

Examples of resin beads 48 include beads functionalized with one or more ligands selected from Protein A, Protein G, Protein NG, and Protein L, among other affinity ligands. Specific examples of Protein A ligands are described in U.S. Pat. No. 5,580,788 entitled "Use of immunoglogulin-binding artificial proteins as molecular weight markers".

The resin beads 48 may be combined with the permeate containing the target protein 44 using any suitable apparatus 45 such as a mixing tank or in-line static mixer. Combining the permeate with the resin beads 48 results in a fluid which contains resin beads 48 with bound target protein 44, as well as cell debris 42 and other components including metabolic waste (not illustrated).

Figure 4:
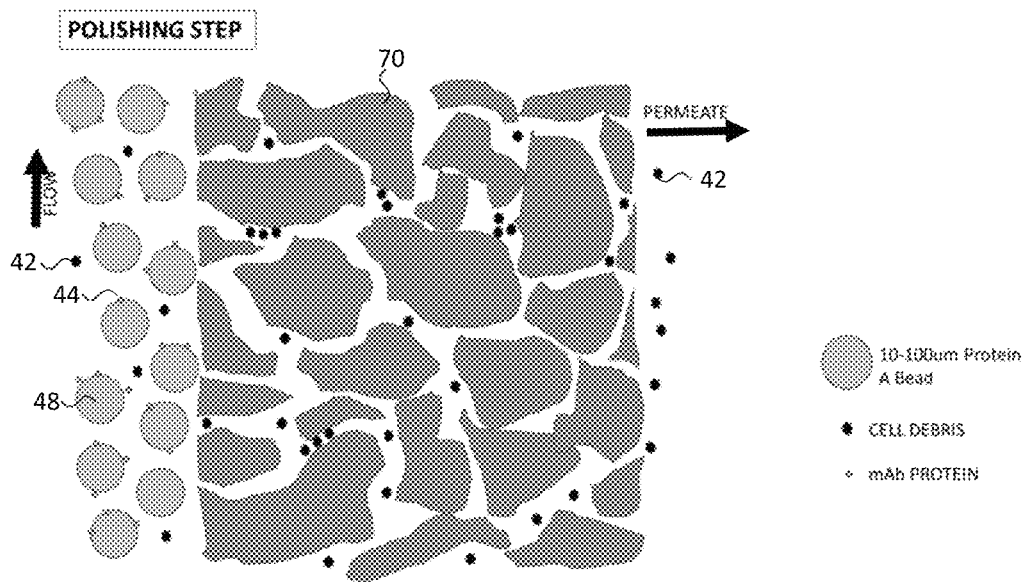
FIG. 4 is a schematic partial cross-sectional view of a wall of a hollow fiber within a tangential flow filter during a second filtration stage.

As illustrated in FIG. 4, this fluid is passed through a second tangential flow filter to separate the resin beads 48 with bound target protein 44, which flow along the surface of a filter wall 70 and emerge from the second tangential flow filter in a second retentate that is subjected to further processing, from the cell debris 42 (as well as other components including metabolic waste, not illustrated), which passes through the filter wall 70 via pores in the filter wall to form a second permeate, which may be discarded.

Any filtration system may be used as well, so long as the filtration system is able to separate the resin beads 48 with bound target protein 44 from the cell debris 42. In certain embodiments, a second tangential flow filter employing thick wall hollow fibers having mean pore sizes ranging from 1 μm to 30 μm, typically ranging from 6 μm to 20 μm (e.g., a pore size that allows the cell debris 10 to pass through the filter wall 70 without plugging, while at the same time holding back the resin beads 48 with bound target protein 44). In certain embodiments, a filter having a pore size that that is about ⅓ times the diameter of the resin beads 48 while also being large enough for the cell debris 10 to pass through the filter wall 70 without clogging is used. In certain embodiments, a second tangential flow filter employing thick wall hollow fibers having an inner lumen diameter ranging from 1 mm to 7 mm, typically about 1 mm to 2 mm, and a wall thickness of 1 mm to 8 mm, typically about 2 mm to 3 mm, may be employed.

Although a single second tangential flow filter is described above for the second filtration stage, multiple filters may also be provided at this stage. For example, multiple filters may be provided in parallel to increase capacity and/or in series to ensure that effectively all of the cell debris 42 is removed. Where placed in series, the pore size of the multiple filters may be constant or the pore size of the multiple filters may change as one proceeds downstream. In this regard, in certain embodiments, the pore size of the multiple filters may increase as one proceeds downstream for instance the first filter might be tighter at 0.5 um or 2.0 um to preclude any rapid uptake of cell debris into the wall and premature filter fouling. The next filters in series might be 2.0 um to 20.0 um.

Figure 5:
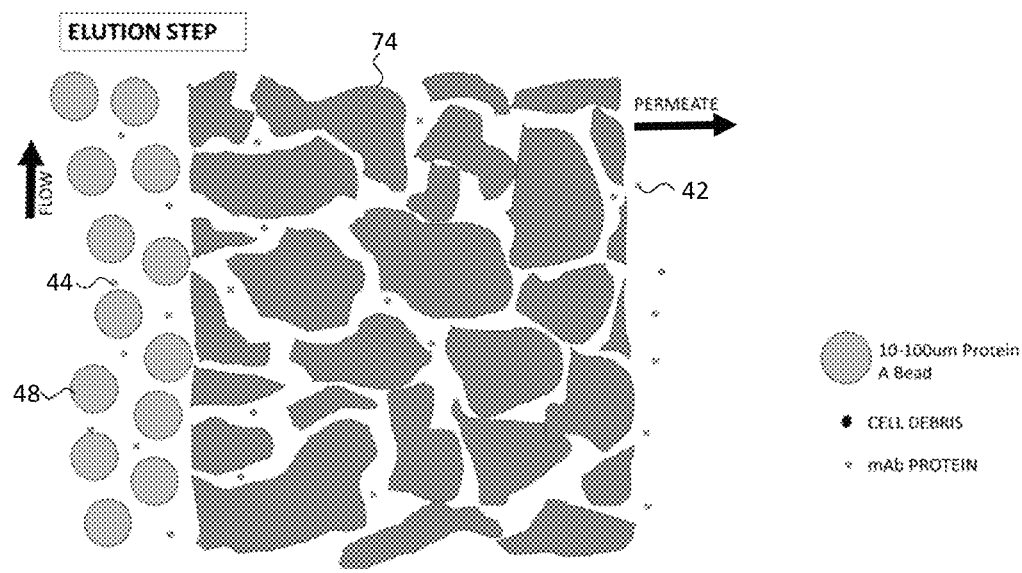
FIG. 5 is a schematic partial cross-sectional view of a wall of a hollow fiber within a tangential flow filter like during a third filtration stage.

Turning now to FIG. 5, in a third stage, retentate from the second tangential flow filtration process, which contains the resin beads 48 with bound target protein 44, is first combined with a suitable elution buffer to release is target protein 44 from the resin beads 48, followed by filtration in a third tangential flow filter, to separate the resin beads 48 from the target protein 44. The elution buffer may be combined with the resin beads 48 using any suitable apparatus such as a mixing tank or in-line static mixer. A variety of elution buffers may be employed at this stage, which typically cause the target protein 44 to become unbound from the resin beads 48 via a decrease in pH and/or an increase in salt (e.g., NaCl, KCl, etc.) concentration. Higher salt concentrations allow more neutral pH conditions to be employed, which may be less likely to cause denaturation and inactivation of the target protein. In general, elution conditions are chosen under which the antibody is stable in order not to lose biological activity. Exemplary buffer solutions for this step include citric acid, glycine HCL or other acidic buffers. In certain embodiments, a volume of buffer may be added to make up for the loss of permeate in the second tangential flow filtration process.

Combining the retentate from the second tangential flow filtration process with the elution buffer results in a fluid which contains resin beads 48 and unbound target protein 44. At this point, the fluid is passed through a filtration system that is able to separate the resin beads 48 from the target protein 44. As illustrated in FIG. 4, the fluid is passed through a third tangential flow filter to separate the resin beads 48, which flow along the surface of the filter wall 70 and emerge from the third tangential flow filter in a third retentate, from the target protein 44 which passes through the filter wall 70 via pores in the filter wall 70 to form a third permeate. The third tangential flow filter generally has a pore size that allows the target protein 44 to pass through the filter wall 70 while at the same time holding back the resin beads 48. As above, a filter may be selected, which has a pore size that that is about ⅓ times the size of the diameter of the resin beads 48. In certain embodiments, a third tangential flow filter employing thick wall hollow fibers having a mean pore size ranging from 1 μm to 30 μm, typically ranging from 2 μm to 8 μm may be employed. In certain embodiments, a third tangential flow filter employing thick wall hollow fibers having an inner lumen diameter ranging from 1 mm to 7 mm, typically about 1 mm to 2 mm, and a wall thickness of 1 mm to 8 mm, typically about 2 mm to 3 mm may be employed. However, as noted above, other filtration systems may be used as well, so long as the filtration system is able to separate the resin beads 48 from the target protein 44. Because the target protein 44 is much smaller than the resin beads 48, a standard 0.2 μm to 0.65 um tangential flow filter could also be used at this step.

The third permeate, which contains the target protein 44 may be subjected to further processing. For example, the target protein 44 may be subject to further processing including concentration, further chromatography steps, buffer exchanges, and so forth.

Moreover, if desired the third retentate may subjected to further processing to regenerate the resin beads 48. For example, the resin beads 48 may be regenerated by a sodium hydroxide wash.

Two systems will now be described which can be used to perform the above-described method.

Figure 6:
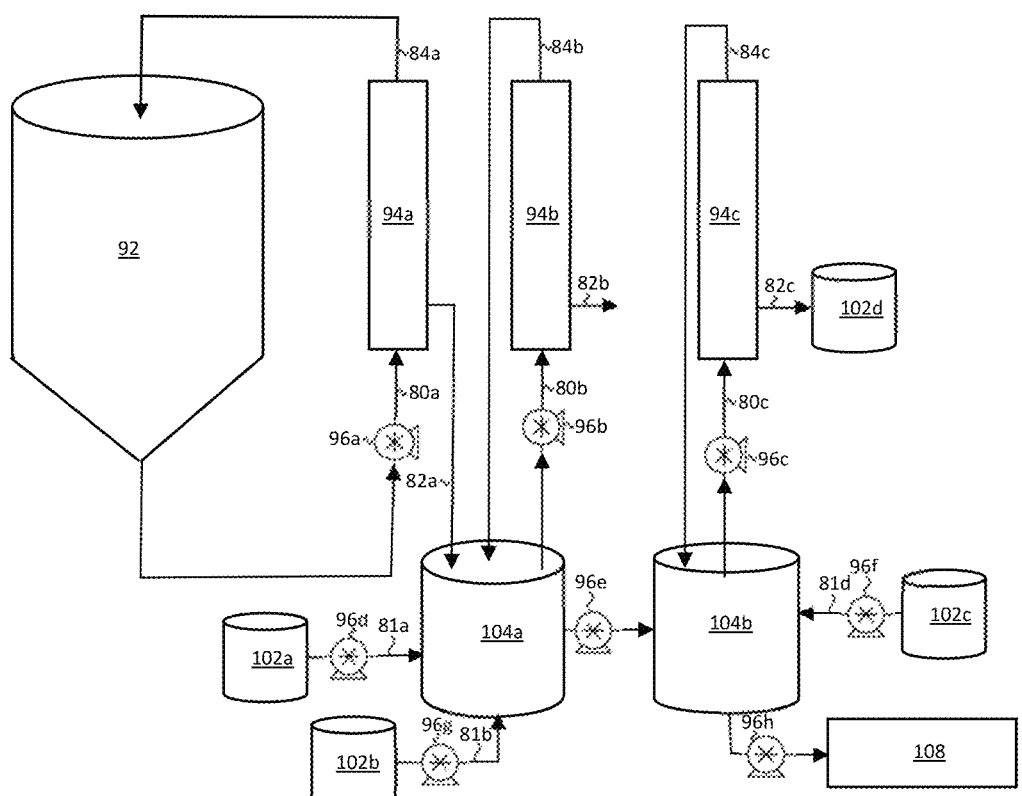
FIG. 6 is a schematic illustration of a bioreactor and batch processing system, in accordance with an embodiment of the present disclosure.

Turning now to FIG. 6, a batch processing system is shown which includes a bioreactor vessel 92, tangential flow filters 94a, 94b, 94c, storage tanks 102a, 102b, 102c, 102d, 102e, mixing tanks 104a, 104b, 104b, 104c, 104d, pumps 96a, 96b, 96c, 96d, 96e, 96f, 96g, 96h, and a resin regeneration unit 108.

In certain embodiments, the system shown may be operated as follows. In a first filtration stage, fluid stream 80a that comprises cells, cell debris, and targeted product produced by the cells in bioreactor 92 is pumped by pump 96a from the bioreactor 92 and into a fluid inlet port of a first tangential flow filter 94a. Once introduced into the first tangential flow filter 94a, the fluid stream 80a, which contains cells, cell debris, targeted product, and waste products is separated by the first tangential flow filter 94a into a first retentate stream 84a comprising the cells (as well as a reduced amount of cell debris, targeted product and waste products), which exits the first tangential flow filter 94a through a first retentate outlet port and flows back into the bioreactor 92, and a first permeate stream 82a comprising the targeted product, cell debris and waste products, which exits the first tangential flow filter 94a through a first permeate outlet port and flows into a first mixing tank 104a. As the first permeate stream 82a exits the first tangential flow filter 94a, cells are concentrated in the first retentate stream 84a and thus the bioreactor vessel 92. In some embodiments, it may be desirable to add an additional washing solution (e.g., media or a buffer solution such as phosphate buffer saline) either to the fluid stream 80a entering the first tangential flow filter 94a or to the first permeate stream 82a exiting the first tangential flow filter 94a (typically to the first permeate stream 82a exiting the first tangential flow filter 94a), to increase the volume of the stream that is returned to the bioreactor vessel 92 and to wash the smaller particles including the target protein, virus or other smaller particles out of the bioreactor vessel 92.

A resin stream 81a containing resin beads that have an affinity for the targeted product is pumped from storage tank 102a via pump 96d and into mixing tank 104a where it is mixed with the first permeate stream 82a (the first permeate stream 82a and resin stream 81a can proceed sequentially or concurrently), resulting in a first fluid mixture which contains resin-bound target product, cell debris and waste product.

In a second filtration stage, a fluid stream 80b of the first fluid mixture is then pumped by pump 96b from the mixing tank 104a and into an inlet port of a second tangential flow filter 94b. Once introduced into second tangential flow filter 94b, the fluid stream 80b, which contains the resin-bound target product, cell debris and waste product, is separated by the second tangential flow filter 94b into a second retentate stream 84b comprising resin-bound target product and reduced amounts of cell debris and waste products, which exits the second tangential flow filter 94b via a retentate outlet port, and a second permeate stream 82b containing cell debris and waste products which exits the second tangential flow filter 94b through a second permeate outlet port. The second permeate stream 82b containing cell debris and waste products can be treated and/or disposed of as appropriate. The second retentate stream 84b flows back to the first mixing tank 104a. Over time this process will produce resin-bound target product having depleted amounts of cell debris and waste.

Optionally, the amounts of cell debris and waste associated with the resin-bound target product may be further depleted by the introduction of a washing solution. In this regard, a washing stream 81*b*, which contains a washing solution, may be pumped by pump 96*g* from a storage tank 102*b* into the mixing tank 104*a*. Examples of suitable washing solutions include phosphate buffered saline.

In some embodiments, the washing solution is introduced during the course of the second filtration phase described above. In these embodiments, the amount of washing solution added may be equal to the amount of permeate removed by the second permeate stream 82*b*, thereby keeping the volume in the mixing tank 104*a* constant. In other embodiments, the amount of washing solution added is less than or greater than the amount of permeate removed by the second permeate stream 82*b*.

As another option, in an optional washing stage, the washing solution may be introduced after the second filtration stage described above. In this regard, a washing stream 81*b*, which contains a washing solution, may be pumped pump 96*g* from a storage tank 102*b* into the mixing tank 104*a* where it is mixed with the fluid produced during the course of the second filtration phase, which contains the resin-bound target product and depleted amounts of cell debris and waste product. The amount of washing solution may vary and may be less than, equal to, or greater than the amount of permeate previously removed by the second permeate stream 82*b*.

Then, a fluid stream 80*b* which contains the resin-bound target product, depleted amounts of cell debris, waste products and washing solution may be pumped by pump 96*b* from the mixing tank 104*a* and into the inlet port of the second tangential flow filter 94*b*. Once re-introduced into the second tangential flow filter 94*b*, the fluid stream 80*b* is separated by the second tangential flow filter 94*b* into a second retentate flow comprising resin-bound target product and further reduced amounts of cell debris and waste products (as well as reduced amounts of the washing solution), which exits the second tangential flow filter 94*b* via the retentate outlet port, and a second permeate stream 82*b* containing cell debris and waste products (as well as portion of the washing solution) which exits the second tangential flow filter 94*b* through the second permeate outlet port. The second permeate stream 82*b* can be treated and/or disposed of as appropriate. The second retentate stream 84*b* flows back to the first mixing tank 104*a*. Over time, this process will produce resin-bound target product having even further depleted amounts of cell debris and waste. While the second tangential flow filter 94*b* is reused in this washing process, it should be noted that a different tangential flow filter may be used in this process if desired.

Regardless of whether or not a washing solution is added, once the desired amount of cell debris and waste have been separated from the resin-bound target product, the resin-bound target product is then subjected to a third filtration stage. In the embodiment shown, resin-bound target product pumped via pump 96*e* from mixing tank 104*a* to another mixing tank 104*b* (in other embodiments, the same mixing tank 104*a* can be used). An elution stream 81*d*, which contains an elution buffer, may also be pumped by pump 96*f* from a storage tank 102*c* into the mixing tank 104*b*. The elution buffer can be added to the mixing tank 104*a* before, after, or concurrently with the addition of the resin-bound target product. As noted above, the elution buffer selected is one that causes the targeted product to become unbound from the resin beads.

A fluid stream 80*c*, which contains the resin beads and unbound target product, is then pumped by pump 96*c* from the mixing tank 104*b* and into an inlet port of a third tangential flow filter 94*c*.

Once introduced into third tangential flow filter 94*c*, the fluid stream 80*c* is separated by the third tangential flow filter 94*c* into a third retentate stream 82*c* comprising resin beads, which exits the third tangential flow filter 94*c* via a retentate outlet port and is returned to the second mixing tank 104*b*, and a third permeate stream 82*c* comprising targeted product which exits the third tangential flow filter to be stored in storage tank 102*d*. Over time, this process will produce resin beads having substantially depleted amounts of targeted product. At this point the resin beads may either be discarded or pumped by pump 96*h* from the mixing tank 104*b* into a resin regeneration unit 108. Once regenerated, the regenerated resin beads can be placed in storage tank 102*a* for reuse.

Figure 7:
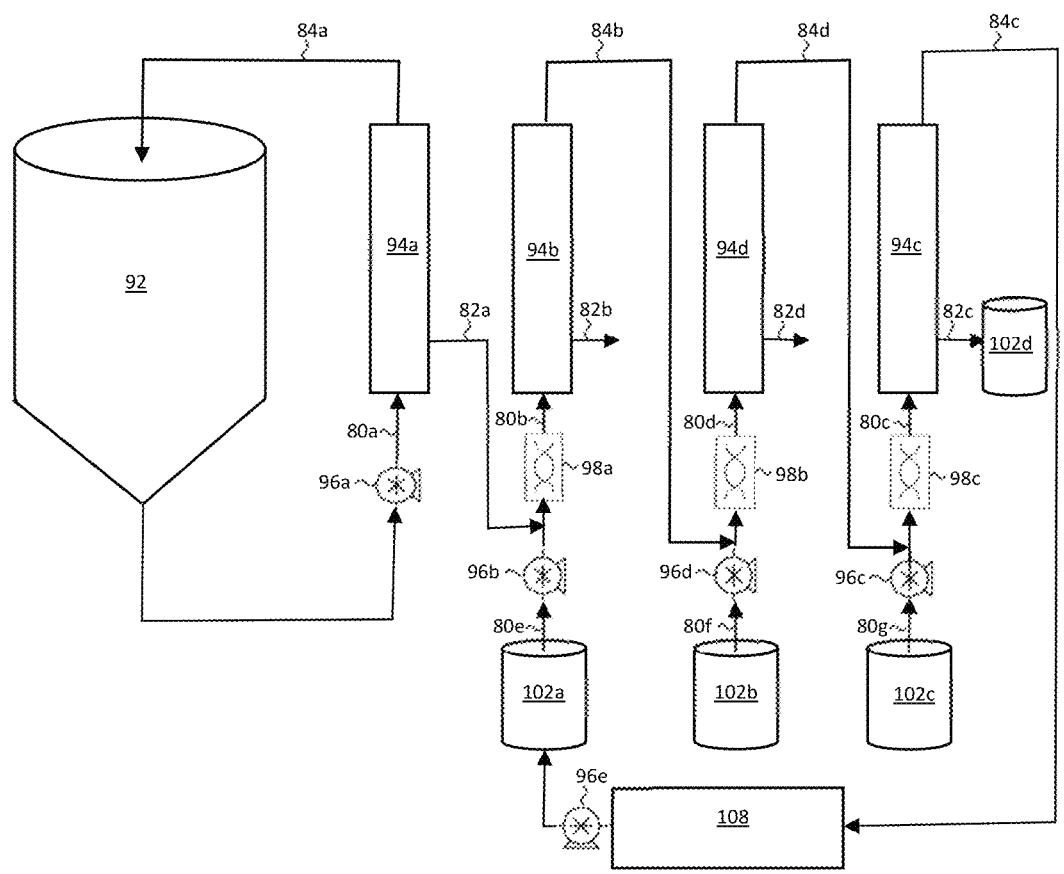
FIG. 7 is a schematic illustration of a bioreactor and continuous processing system, in accordance with an embodiment of the present disclosure.

Turning now to FIG. 7, a continuous processing system is shown which includes a bioreactor vessel 92, tangential flow filters 94*a*, 94*b*, 94*c*, 94*d*, storage tanks 102*a*, 102*b*, 102*c*, 102*d*, pumps 96*a*, 96*b*, 96*c*, 96*d*, 96*e*, and a resin regeneration unit 108.

In certain embodiments, the system may be operated as follows. In a first filtration stage, a fluid stream 80*a* that comprises cells, cell debris, waste products and a targeted product produced by the cells in bioreactor 92 is pumped by pump 96*a* from the bioreactor 92 and into an inlet port of a first tangential flow filter 94*a*. Once introduced into the first tangential flow filter 94*a*, the fluid stream 80*a*, which contains cells, cell debris, waste products and targeted product, is separated by the first tangential flow filter 94*a* into a first retentate stream 84*a* comprising the cells (as well as a reduced amount of cell debris, waste products and targeted product), which exits the first tangential flow filter 94*a* through a first retentate outlet port and flows through back into the bioreactor 92, and a first permeate stream 82*a* comprising the targeted product, cell debris and waste products which exits the first tangential flow filter 94*a* through a first permeate outlet port.

At the same time that the first permeate stream 82*a* exits the first tangential flow filter 94*a*, a resin stream 80*e* containing resin beads that have an affinity for the targeted product is pumped from storage tank 102*a* via pump 96*b*. The resin stream 80*e* is combined with the first permeate stream 82*a* and introduced into a static mixer 98*a*, resulting in a fluid stream 80*b* which contains resin-bound target product, cell debris and waste products.

In a second filtration stage, the fluid stream 80*b* is then is then introduced into an inlet port of a second tangential flow filter 94*b*. Once introduced into second tangential flow filter 94*b*, the fluid stream 80*b*, which contains the resin-bound target product, cell debris and waste product, is separated by the second tangential flow filter 94*b* into a second retentate stream 84*b* comprising resin-bound target product and reduced amounts of cell debris and waste products, which exits the second tangential flow filter 94*b* via a retentate outlet port, and a second permeate stream 82*b* containing cell debris and waste products which exits the second tangential flow filter 94*b* through a second permeate outlet port. The second permeate stream 82*b* containing cell debris and waste products can be treated and/or disposed of as appropriate.

In the embodiment shown, the second retentate stream 84*b* comprising resin-bound target product and reduced amounts of cell debris and waste products is, in an optional washing stage, washed in a further tangential flow filter 94d to further reduce the amounts of cell debris and waste products.

In this regard, at the same time the second retentate stream 84b exits the second tangential flow filter 94b, a washing stream 80f, which contains a washing solution, is pumped from storage tank 102b via pump 96d. The washing stream 80f is combined with the second retentate stream 84b and introduced into a static mixer 98b, resulting in a combined fluid stream 80d which contains resin-bound target product, cell debris, waste products and washing solution.

The combined fluid stream 80d, which contains resin-bound target product, cell debris, waste products and washing solution is then introduced into an inlet port of a further tangential flow filter 94d. Once introduced into the tangential flow filter 94d, the combined fluid stream 80d is separated by the tangential flow filter 94d into a further retentate stream 84d comprising resin-bound target product and further reduced amounts of cell debris and waste products (as well as a portion of the washing solution), which exits the tangential flow filter 94d via a further retentate outlet port, and a further permeate stream 82d containing cell debris and waste products (as well as portion of the washing solution) which exits the tangential flow filter 94d through a further permeate outlet port. The permeate stream 82d containing cell debris and waste products can be treated and/or disposed of as appropriate.

Once the desired amount of cell debris and waste have been separated from the resin-bound target product (e.g., by providing no additional washing stage or by providing one, two or more washing stages), the retentate containing the resin-bound target product (in FIG. 6 the further retentate stream 84d) is then subjected to further processing to separate the target product from the resin beads.

In the example shown, at the same time the further retentate stream 84d exits the further tangential flow filter 94d, an elution stream 80g, which contains a suitable elution buffer, is pumped from storage tank 102c via pump 96c. The further retentate stream 84d containing the resin-bound target product is combined with the elution stream 80g (which causes the target product to be unbound from the resin beads) and introduced into a static mixer 98c, resulting in a combined fluid stream 80c which comprises resin beads and target product (and elution buffer).

In a third filtration stage, the combined fluid stream 80c, which contains resin beads and target product is then introduced into an inlet port of a third tangential flow filter 94c. Once introduced into third tangential flow filter 94c, the combined fluid stream 80c is separated by the third tangential flow filter 94c into a third retentate stream 84c comprising the resin beads, which exit the third tangential flow filter 94c via a third retentate outlet port, and a third permeate stream 82c containing target product which exits the third tangential flow filter 94c through a third permeate outlet port, whereupon it is stored in storage tank 102d.

At this point the resin beads in the third retentate stream 84c may either be discarded or routed into a resin regeneration unit 108. Once regenerated, the regenerated resin beads can be pumped by pump 96e into storage tank 102a, where in can be reused in the process.

Additional features of the present disclosure are set forth in the following enumerated aspects:

Aspect 1. A filtration method comprising: (a) passing a first fluid that comprises cells, cell debris and a targeted product produced by the cells through a first filter such that the first fluid is separated by the first filter into a first retentate comprising the cells and a first permeate comprising the targeted product and a first portion of the cell debris that passes through the first filter; (b) combining resin beads having affinity for the targeted product with the first permeate such that a second fluid is formed that comprises the resin beads with bound target product and the first portion of the cell debris; and (c) passing the second fluid through a second filter such that the second fluid is separated by the second filter into a second retentate comprising the resin beads with the bound target product and second permeate comprising a second portion of the cell debris that passes through the second filter.

Aspect 2. The method of aspect 1, further comprising combining an elution buffer with the second retentate such that the targeted product becomes unbound from the resin beads and a third fluid is formed that comprises a mixture of the resin beads and the targeted product; and passing the third fluid through a third filter such that the third fluid is separated by the third filter into a third retentate comprising the resin beads and a third permeate comprising the targeted product.

Aspect 3. The method of any of aspects 1-2, wherein the second retentate is directly combined with the elution buffer.

Aspect 4. The method of aspect 3, further comprising washing the second retentate by a process wherein the second retentate is mixed with a washing solution and subjected to additional filtration to further reduce the amount of cell debris in the second retentate before combining with the elution buffer.

Aspect 5. The method of any of aspects 1-4, wherein the process is a batch process.

Aspect 6. The method of aspect 5, wherein the resin beads and the first permeate are combined in a first batch mixer, wherein the elution buffer and the second retentate are combined in a second batch mixer, or both.

Aspect 7. The method of any of aspects 1-4, wherein the process is a continuous process.

Aspect 8. The method of aspect 7, wherein the second fluid is passed through a first static mixer prior to passage through the second filter, wherein third fluid is passed through a third static mixer prior to passage through the second filter, or both.

Aspect 9. The method of any of aspects 2-8, further comprising regenerating the resin beads in the third retentate.

Aspect 10. The method of any of aspects 1-9, wherein the targeted product is a protein.

Aspect 11. The method of any of aspects 1-9, wherein the targeted product a monoclonal antibody or a polyclonal antibody.

Aspect 12. The method of any of aspects 1-11, wherein the resin beads are functionalized with one or more ligands selected from Protein A, Protein G, Protein NG, and Protein L.

Aspect 13. The method of any of aspects 1-12, wherein the first filter has a mean pore size ranging from 1 µm to 8 µm.

Aspect 14. The method of any of aspects 1-13, wherein the first filter is a first tangential flow filter.

Aspect 15. The method of aspect 14, wherein the first tangential flow filter comprises hollow fibers having an inner lumen diameter ranging from 1 mm to 7 mm and a wall thickness of 1 mm to 8 mm.

Aspect 16. The method of any of aspects 1-15, wherein the second filter has a mean pore size ranging from 2 µm to 30 µm.

Aspect 17. The method of any of aspects 1-16, wherein the second filter is a second tangential flow filter.

Aspect 18. The method of aspect 17, wherein the second tangential flow filter comprises hollow fibers having an inner lumen diameter ranging from 1 mm to 7 mm and a wall thickness of 1 mm to 8 mm.

Aspect 19. The method of any of aspects 2-18, wherein the third filter has a mean pore size ranging from 2 μm to 30 μm.

Aspect 20. The method of any of aspects 2-19, wherein the third filter is a third tangential flow filter.

Aspect 21. The method of aspect 20, wherein the third tangential flow filter comprises hollow fibers having an inner lumen diameter ranging from 1 mm to 7 mm and a wall thickness of 1 mm to 8 mm.

While the disclosure herein disclosed has been described by means of specific aspects, embodiments and applications thereof, numerous modifications and variations could be made thereto by those skilled in the art without departing from the scope of the disclosure set forth in the claims.

The invention claimed is:

1. A filtration method comprising:
    passing a first fluid that comprises cells, cell debris and a targeted product produced by the cells through a first filter such that the first fluid is separated by the first filter into a first retentate comprising the cells and a first permeate comprising the targeted product and a first portion of the cell debris that passes through the first filter;
    combining resin beads having affinity for the targeted product with the first permeate such that a second fluid is formed that comprises the resin beads with bound target product and the first portion of the cell debris;
    passing the second fluid through a second filter such that the second fluid is separated by the second filter into a second retentate comprising the resin beads with the bound target product and second permeate comprising a second portion of the cell debris that passes through the second filter;
    unbinding the targeted product from the resin beads with the bound targeted product such that a third fluid is formed that comprises a mixture of the resin beads and the targeted product; and
    passing the third fluid through a third filter such that the third fluid is separated by the third filter into a third retentate comprising the resin beads and a third permeate comprising the targeted product.

2. The method of claim 1, further comprising combining an elution buffer with the second retentate such that the targeted product becomes unbound from the resin beads with the bound targeted product to form the third fluid.

3. The method of claim 2, wherein the second retentate is directly combined with the elution buffer.

4. The method of claim 3, further comprising washing the second retentate by a process wherein the second retentate is mixed with a washing solution and subjected to additional filtration to further reduce the amount of cell debris in the second retentate before combining with the elution buffer.

5. The method of claim 1, wherein the filtration method is a batch process.

6. The method of claim 5, wherein the resin beads and the first permeate are combined in a first batch mixer, wherein an elution buffer and the second retentate are combined in a second batch mixer, or both.

7. The method of claim 1, wherein the filtration method is a continuous process.

8. The method of claim 7, wherein the second fluid is passed through a first static mixer prior to passage through the second filter, wherein the third fluid is passed through a second static mixer prior to passage through the third filter, or both.

9. The method of claim 1, further comprising regenerating the resin beads in the third retentate.

10. The method of claim 1, wherein the targeted product is a protein.

11. The method of claim 1, wherein the targeted product is a monoclonal antibody or a polyclonal antibody.

12. The method of claim 1, wherein the resin beads are functionalized with one or more ligands selected from Protein A, Protein G, Protein A/G, and Protein L.

13. The method of claim 1, wherein the first filter has a mean pore size ranging from 1 μm to 8 μm.

14. The method of claim 1, wherein the first filter is a first tangential flow filter.

15. The method of claim 14, wherein the first tangential flow filter comprises hollow fibers having an inner lumen diameter ranging from 1 mm to 7 mm and a wall thickness of 1 mm to 8 mm.

16. The method of claim 1, wherein the second filter has a mean pore size ranging from 2 μm to 30 μm.

17. The method of claim 1, wherein the second filter is a second tangential flow filter.

18. The method of claim 17, wherein the second tangential flow filter comprises hollow fibers having an inner lumen diameter ranging from 1 mm to 7 mm and a wall thickness of 1 mm to 8 mm.

19. The method of claim 1, wherein the third filter has a mean pore size ranging from 2 μm to 30 μm.

20. The method of claim 1, wherein the third filter is a third tangential flow filter.

21. The method of claim 20, wherein the third tangential flow filter comprises hollow fibers having an inner lumen diameter ranging from 1 mm to 7 mm and a wall thickness of 1 mm to 8 mm.

* * * * *